(12) United States Patent
Kadokura (10) Patent No.: US 11,666,402 B2
(45) Date of Patent: Jun. 6, 2023

(54) END EFFECTOR FORCE FEEDBACK TO MASTER CONTROLLER

(71) Applicant: Intuitive Surgical Operations, Inc., Sunnyvale, CA (US)

(72) Inventor: Grant M. Kadokura, San Diego, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 392 days.

(21) Appl. No.: 16/753,298

(22) PCT Filed: Oct. 2, 2018

(86) PCT No.: PCT/US2018/053998
§ 371 (c)(1),
(2) Date: Apr. 2, 2020

(87) PCT Pub. No.: WO2019/070734
PCT Pub. Date: Apr. 11, 2019

(65) Prior Publication Data
US 2020/0237461 A1 Jul. 30, 2020

Related U.S. Application Data (60) Provisional application No. 62/567,005, filed on Oct. 2, 2017.

(51) Int. Cl.
*A61B 34/35* (2016.01)
*A61B 34/37* (2016.01)
(Continued)

(52) U.S. Cl.
CPC ............. *A61B 34/37* (2016.02); *A61B 34/35* (2016.02); *A61B 17/00234* (2013.01);
(Continued)

(58) Field of Classification Search
CPC ............. A61B 34/37; A61B 34/35; A61B 17/00234; A61B 34/71; A61B 34/76; A61B 2017/2927; A61B 2034/305
(Continued)

(56) References Cited

U.S. PATENT DOCUMENTS

| 4,604,016 A | 8/1986 | Joyce |
| 5,116,180 A | 5/1992 | Fung et al. |

(Continued)

FOREIGN PATENT DOCUMENTS

| CN | 203092570 U | 7/2013 |
| EP | 2023844 A2 | 2/2009 |

(Continued)

OTHER PUBLICATIONS

International Preliminary Report on Patentability for Application No. PCT/US2018/053998, dated Apr. 16, 2020, 14 pages.

(Continued)

*Primary Examiner* — Jaime Figueroa (57) ABSTRACT

A teleoperated surgical system is provided that includes a surgical instrument that includes an end effector mounted for rotation about a slave pivot axis; a master control input includes a mount member, first and second master grip rotatably secured at the mount member for rotation about a master pivot axis; sensor to produce a sensor signal indicative of a slave grip counter-force about the slave pivot axis; one or more motors to impart a shear force to the mount member, perpendicular to the master pivot axis; one or more processors to convert the sensor signal to motor control signals to cause the motors to impart the feedback shear force to the first and second master grip members.

20 Claims, 9 Drawing Sheets

(51) Int. Cl.
*A61B 34/00* (2016.01)
*A61B 34/30* (2016.01)
*A61B 17/00* (2006.01)
*A61B 17/29* (2006.01)

(52) U.S. Cl.
CPC .............. *A61B 34/71* (2016.02); *A61B 34/76* (2016.02); *A61B 2017/00398* (2013.01); *A61B 2017/00477* (2013.01); *A61B 2017/2927* (2013.01); *A61B 2034/305* (2016.02)

(58) Field of Classification Search
USPC ................. 700/245–264; 318/568.11–568.25
See application file for complete search history.

(56) References Cited

U.S. PATENT DOCUMENTS

| | | | |
|---|---|---|---|
| 5,696,837 A | 12/1997 | Green | |
| 5,710,870 A * | 1/1998 | Ohm | B25J 19/02 700/262 |
| 5,784,542 A * | 7/1998 | Ohm | A61B 34/35 901/34 |
| 6,024,576 A | 2/2000 | Bevirt et al. | |
| 6,102,850 A | 8/2000 | Wang et al. | |
| 6,184,868 B1 | 2/2001 | Shahoian et al. | |
| 6,197,017 B1 * | 3/2001 | Brock | A61B 34/30 414/730 |
| 6,377,011 B1 * | 4/2002 | Ben-Ur | G06F 3/016 345/184 |
| 6,385,509 B2 | 5/2002 | Das et al. | |
| 6,459,926 B1 | 10/2002 | Nowlin et al. | |
| 6,587,750 B2 | 7/2003 | Gerbi et al. | |
| 6,594,552 B1 | 7/2003 | Nowlin et al. | |
| 6,671,581 B2 | 12/2003 | Niemeyer et al. | |
| 6,714,839 B2 * | 3/2004 | Salisbury, Jr. | A61B 34/35 901/14 |
| 6,723,106 B1 | 4/2004 | Charles et al. | |
| 6,817,974 B2 | 11/2004 | Cooper et al. | |
| 6,994,703 B2 * | 2/2006 | Wang | A61B 34/75 606/7 |
| 7,248,944 B2 * | 7/2007 | Green | A61B 34/70 348/E13.059 |
| 7,373,219 B2 | 5/2008 | Nowlin et al. | |
| 7,783,383 B2 * | 8/2010 | Eliuk | A61J 3/002 700/214 |
| 7,843,158 B2 | 11/2010 | Prisco | |
| 7,930,066 B2 * | 4/2011 | Eliuk | A61J 3/002 221/9 |
| 8,002,767 B2 | 8/2011 | Sanchez et al. | |
| 8,073,335 B2 | 12/2011 | Labonville et al. | |
| 8,120,301 B2 | 2/2012 | Goldberg et al. | |
| 8,271,130 B2 | 9/2012 | Hourtash et al. | |
| 8,316,961 B2 | 11/2012 | Isobe et al. | |
| 8,343,171 B2 * | 1/2013 | Farritor | A61B 34/73 600/564 |
| 8,423,186 B2 | 4/2013 | Itkowitz et al. | |
| 8,444,631 B2 | 5/2013 | Yeung et al. | |
| 8,479,969 B2 | 7/2013 | Shelton, IV | |
| 8,620,473 B2 | 12/2013 | Diolaiti et al. | |
| 8,644,988 B2 | 2/2014 | Prisco et al. | |
| 8,992,565 B2 | 3/2015 | Brisson et al. | |
| 9,043,019 B2 * | 5/2015 | Eliuk | G07F 11/70 221/9 |
| 9,244,523 B2 | 1/2016 | Ogawa et al. | |
| 9,244,524 B2 | 1/2016 | Inoue et al. | |
| 9,423,869 B2 | 8/2016 | Yanagihara | |
| 9,632,577 B2 | 4/2017 | Ogawa et al. | |
| 9,671,860 B2 | 6/2017 | Ogawa et al. | |
| 9,913,694 B2 | 3/2018 | Brisson | |
| 2001/0018591 A1 * | 8/2001 | Brock | G16H 20/40 606/130 |
| 2003/0060927 A1 | 3/2003 | Gerbi et al. | |
| 2003/0195664 A1 | 10/2003 | Nowlin et al. | |
| 2006/0259195 A1 * | 11/2006 | Eliuk | B01F 33/8442 700/245 |
| 2007/0005002 A1 | 1/2007 | Millman et al. | |
| 2007/0142968 A1 | 6/2007 | Prisco et al. | |
| 2007/0151390 A1 * | 7/2007 | Blumenkranz | A61B 34/71 74/490.06 |
| 2007/0151391 A1 * | 7/2007 | Larkin | A61B 34/76 74/490.06 |
| 2007/0239028 A1 * | 10/2007 | Houser | A61B 34/70 600/471 |
| 2009/0062813 A1 | 3/2009 | Prisco et al. | |
| 2009/0163929 A1 | 6/2009 | Yeung et al. | |
| 2009/0216374 A1 * | 8/2009 | Low | B25J 9/1689 700/258 |
| 2010/0073150 A1 | 3/2010 | Olson et al. | |
| 2010/0256558 A1 | 10/2010 | Olson et al. | |
| 2011/0087238 A1 | 4/2011 | Wang et al. | |
| 2011/0106141 A1 | 5/2011 | Nakamura | |
| 2011/0290856 A1 * | 12/2011 | Shelton, IV | A61B 34/30 227/180.1 |
| 2012/0116391 A1 | 5/2012 | Houser et al. | |
| 2012/0123441 A1 | 5/2012 | Au et al. | |
| 2012/0265051 A1 | 10/2012 | Fischer et al. | |
| 2013/0103050 A1 * | 4/2013 | Richmond | A61B 17/285 606/130 |
| 2013/0172906 A1 | 7/2013 | Olson et al. | |
| 2013/0289767 A1 | 10/2013 | Lim et al. | |
| 2013/0296737 A1 * | 11/2013 | McMillan | A61B 34/30 600/562 |
| 2014/0135793 A1 * | 5/2014 | Cooper | A61B 34/30 901/31 |
| 2014/0330073 A1 * | 11/2014 | Ko | A61B 17/062 606/139 |
| 2014/0371762 A1 | 12/2014 | Farritor et al. | |
| 2015/0360365 A1 | 12/2015 | Fudaba et al. | |
| 2016/0213437 A1 | 7/2016 | Richmond et al. | |
| 2019/0015169 A1 | 1/2019 | Verner et al. | |
| 2019/0142536 A1 * | 5/2019 | Steger | A61B 34/20 606/130 |
| 2019/0201137 A1 * | 7/2019 | Shelton, IV | G16H 70/20 |
| 2020/0278265 A1 | 9/2020 | Suresh | |
| 2020/0330172 A1 | 10/2020 | Farritor et al. | |
| 2021/0093409 A1 * | 4/2021 | Overmyer | B25J 13/085 |

FOREIGN PATENT DOCUMENTS

| | | |
|---|---|---|
| KR | 20150007020 A | 1/2015 |
| WO | WO-2006120666 A1 | 11/2006 |
| WO | WO-2012127404 A2 | 9/2012 |
| WO | WO-2013018934 A1 | 2/2013 |
| WO | WO-2013169303 A1 | 11/2013 |
| WO | WO-2015148293 A1 | 10/2015 |
| WO | WO-2015153642 A1 | 10/2015 |
| WO | WO-2017130562 A1 | 8/2017 |

OTHER PUBLICATIONS

International Search Report and Written Opinion for Application No. PCT/US2018/053998, dated Mar. 14, 2019, 20 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP18865163.2 dated Jun. 11, 2021, 10 pages.
Okamura A.M., "Haptic Feedback in Robot-Assisted Minimally Invasive Surgery," Current Opinion in Urology, 2009, vol. 19 (1), 10 pages.
Office Action for CN Application No. 2018800755690, dated Dec. 19, 2022.

* cited by examiner

END EFFECTOR FORCE FEEDBACK TO MASTER CONTROLLER

RELATED APPLICATIONS

This application is a U.S. National Stage Filing under 35 U.S.C. 371 from International Application No. PCT/US2018/053998, filed on Oct. 2, 2018, and published as WO 2019/070734 A1 on Apr. 11, 2019, which claims the benefit of priority to U.S. Provisional Patent Application Ser. No. 62/567,005, filed on Oct. 2, 2017, each of which is incorporated by reference herein in its entirety.

BACKGROUND

Minimally invasive medical techniques are intended to reduce the amount of tissue that is damaged during diagnostic or surgical procedures, thereby reducing patient recovery time, discomfort, and deleterious side effects. Teleoperated surgical systems that use robotic technology (so-called surgical robotic systems) may be used to overcome limitations of manual laparoscopic and open surgery. Advances in telepresence systems provide surgeons views inside a patient's body, an increased number of degrees of motion of surgical instruments, and the ability for surgical collaboration over long distances. In manual minimally invasive surgery, surgeons feel the interaction of the instrument with the patient via a long shaft, which eliminates tactile cues and masks force cues. In teleoperation surgery systems, natural force feedback is largely eliminated because the surgeon no longer manipulates the instrument directly. Kinesthetic or force feedback systems typically measure or estimate the forces applied to the patient by the surgical instrument.

SUMMARY

In one aspect, a teleoperated surgical system is provided that includes a surgical instrument that includes a shaft, an end effector that includes a first cantilever beam, mounted for rotation about a slave pivot axis disposed at the distal end portion of the shaft. A master control input includes a mount member and a first master grip member mounted upon the mount member for a direction of movement along a first path relative to the mount member. A sensor is configured to sense a magnitude of produce a slave cantilever beam force. One or more actuators are configurable to impart a force to the mount member. One or more processors are configured to cause the one or more acutators to impart a feedback force to the mount member, having a magnitude indicative of the magnitude of the slave cantilever beam force and having a direction of movement along a second path separate from the first path.

In another aspect, a method is provided to provide at a master control input an indication of a grip force at a slave end effector portion mounted to a distal end of a surgical instrument shaft in which the master control input includes a mount member and a first master grip member, mounted for a direction of movement along a first path. The method includes producing a sensor signal indicative of magnitude of a grip moment about a slave pivot axis of the end effector and producing a feedback force at the mount member, having a magnitude based upon the sensor signal and having a direction of movement along a second path separate from the first path.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DESCRIPTION OF EMBODIMENTS

Teleoperated Surgical System

Figure 1:
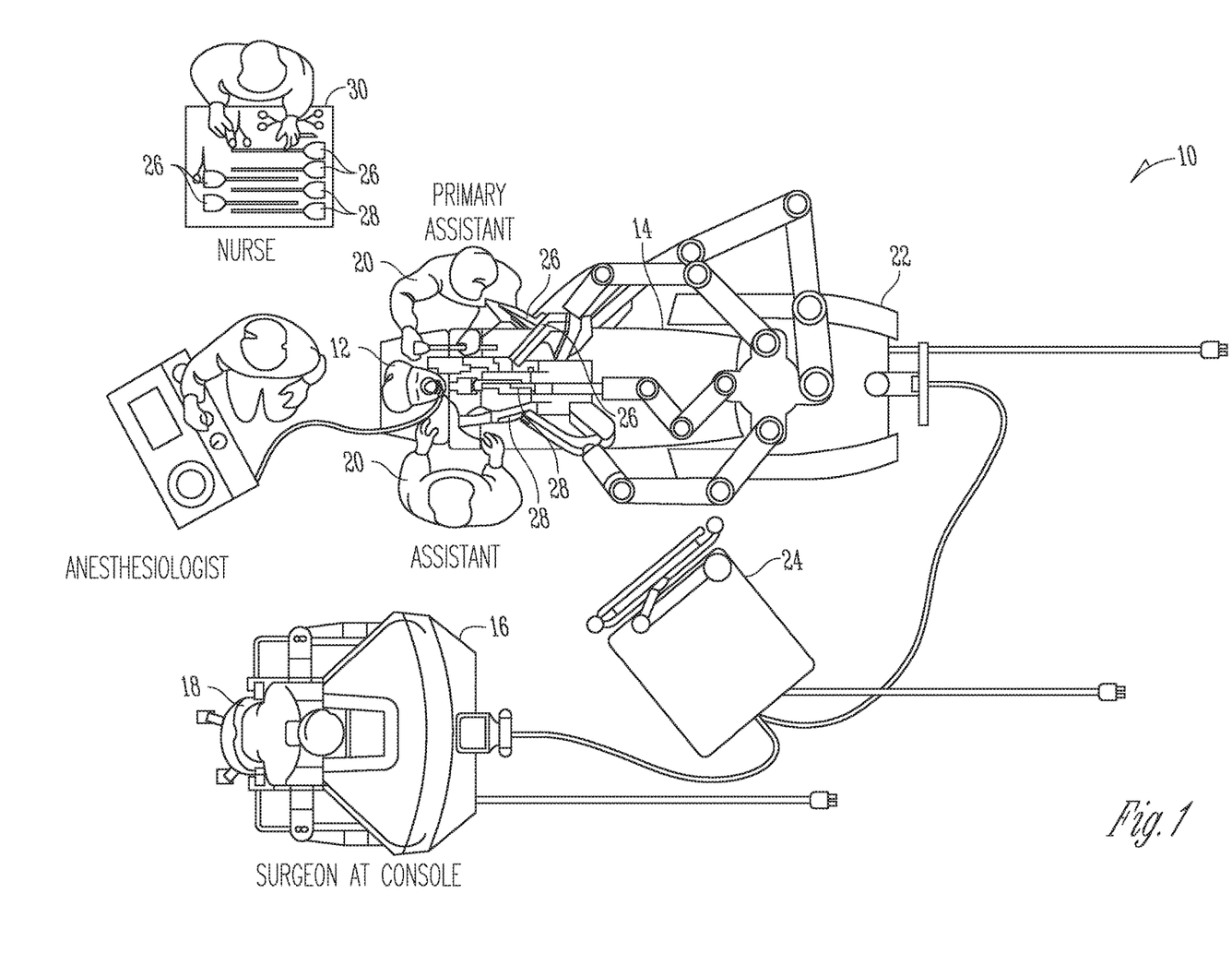
FIG. 1 is an illustrative plan view of a minimally invasive teleoperated surgical system in accordance with some embodiments.

FIG. 1 is an illustrative plan view of a minimally invasive teleoperated surgical system 10 for performing a minimally invasive diagnostic or surgical procedure on a patient 12 who is lying on an operating table 14. The system includes a surgeon's console 16 for use by a surgeon 18 during the procedure. One or more assistants 20 also may participate in the procedure. The minimally invasive teleoperated surgical system 10 further includes one or more patient-side cart (PSC) 22 and an electronics cart 24. The patient-side cart 22 can manipulate at least one surgical instrument 26 through a minimally invasive incision in the body of the patient 12 while the surgeon 18 views the surgical site through the surgeon's console 16. An image of the surgical site can be obtained by an endoscope 28, such as a stereoscopic endoscope, which may be manipulated by the patient-side cart 22 to orient the endoscope 28. Computer processors located on the electronics cart 24 may be used to process the images of the surgical site for subsequent display to the surgeon 18 through the surgeon's console 16. In some embodiments, stereoscopic images may be captured, which allow the perception of depth during a surgical procedure. The number of surgical instruments 26 used at one time will generally depend on the diagnostic or surgical procedure and the space constraints within the operative site among other factors. If it is necessary to change one or more of the surgical instruments 26 being used during a procedure, an assistant 20 may remove the surgical instrument 26 from the patient-side cart 22, and replace it with another surgical instrument 26 from a tray 30 in the operating room.

Figure 2:
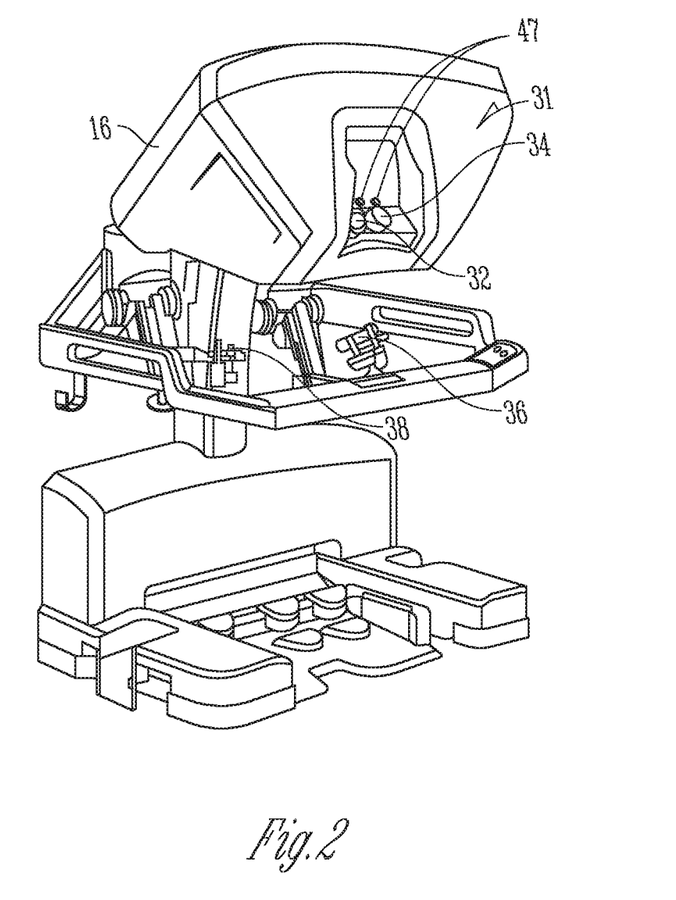
FIG. 2 is a perspective view of the surgeon's console of the system of FIG. 1.

FIG. 2 is a perspective view of the surgeon's console 16. The surgeon's console 16 includes a viewer display 31 that includes a left eye display 32 and a right eye display 34 for presenting the surgeon 18 with a coordinated stereoscopic view of the surgical site that enables depth perception. The console 16 further includes one or more hand-operated control inputs 36 to receive larger-scale hand control movements. One or more surgical instruments installed for use on the patient-side cart 22 move in smaller-scale distances that correspond to a surgeon 18's larger-scale manipulation of the one or more control inputs 36. The control inputs 36 may provide the same mechanical degrees of freedom as their associated surgical instruments 26 to provide the surgeon 18 with telepresence, or the perception that the control inputs 36 are integral with the instruments 26 so that the surgeon has a strong sense of directly controlling the instruments 26. To this end, position, force, and tactile feedback sensors (not shown) may be employed to transmit position, force, and tactile sensations from the surgical instruments 26 back to the surgeon's hands through the control inputs 36, subject to communication delay constraints.

Figure 3:
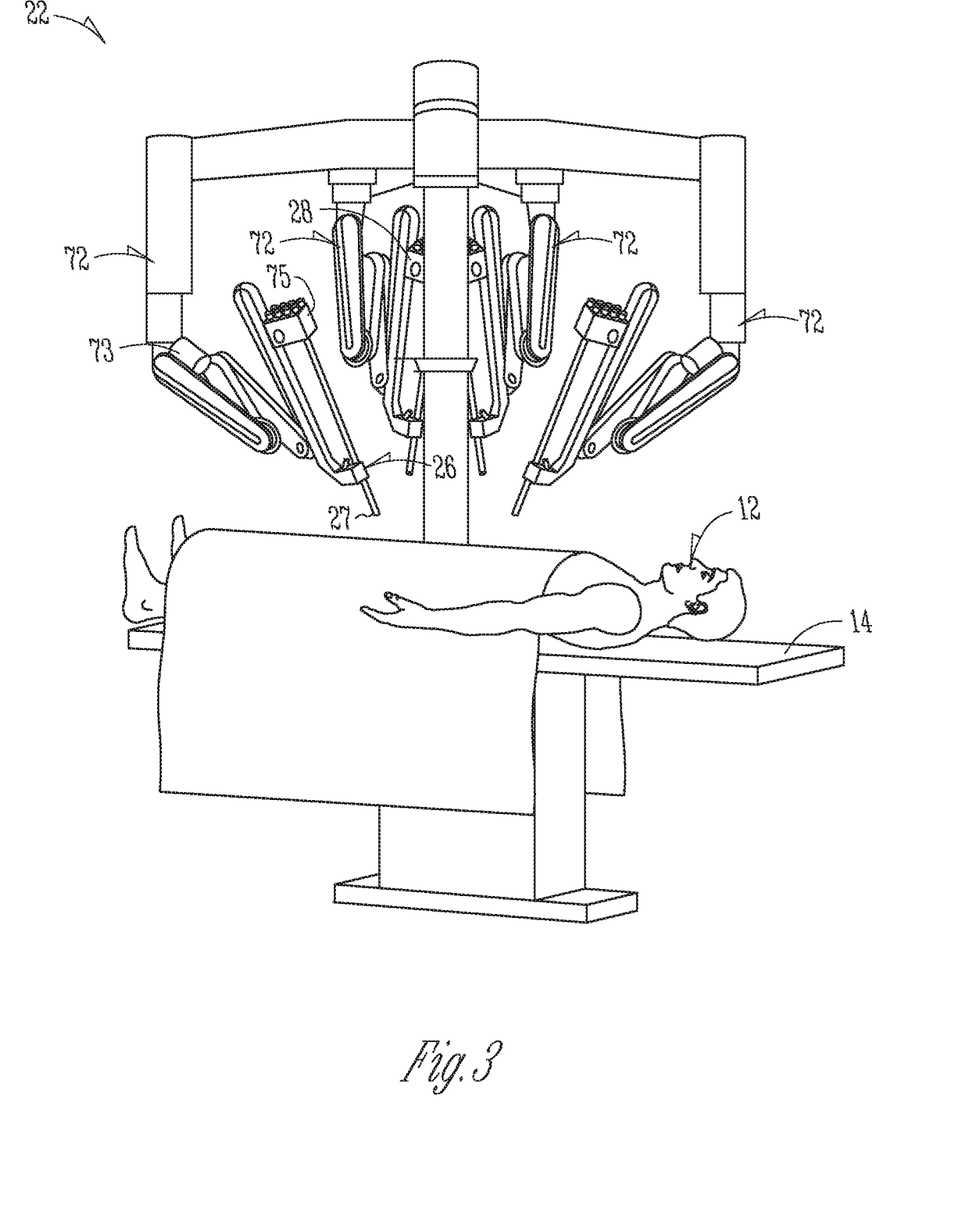
FIG. 3 is a perspective view of a pa t-side cart of the system of FIG. 1.

FIG. 3 is a perspective view of a patient-side cart 22 of a minimally invasive teleoperated surgical system 10, in accordance with some embodiments. The patient-side cart 22 includes four mechanical support arms 72. A surgical instrument manipulator 73, which includes actuators such as motors, to control instrument motion, is mounted at the end of each support arm assembly 72. Additionally, each support arm 72 can optionally include one or more setup joints (e.g., unpowered and/or lockable) that are used to position the attached surgical instrument manipulator 73 in relation to the patient for surgery. While the patient-side cart 22 is shown as including four surgical instrument manipulators 73, more or fewer surgical instrument manipulators 73 may be used. A teleoperated surgical system will generally include a vision system that typically includes an endoscopic camera instrument 28 for capturing video images and one or more video displays for displaying the captured video images.

In one aspect, for example, individual surgical instruments 26 and cannulas 27 are removably coupled to manipulator 73, with the surgical instrument 26 inserted through the cannula 27. One or more teleoperated actuator motors of the manipulator 73 move the surgical instrument 26 as a whole to position it in relation to a patient 12. Each support arm assembly includes an instrument carriage 75. A surgical instrument 26 is detachably connected to an instrument carriage 75. In one aspect, the instrument carriage 75 houses one or more teleoperated actuator motors (not shown) inside that provide a number of controller motions that the surgical instrument 26 translates into a variety of movements of an end effector at a distal end of the surgical instrument 26. Thus, the teleoperated actuator motors within the instrument carriage 75 move individual components of the surgical instrument 26 rather than the instrument as a whole. Inputs to control either the instrument as a whole or the instrument's components are such that the input provided by a surgeon or other medical person to a control input 36 (a "master" command) are translated into a corresponding action by a surgical instrument end effector (a "slave" response). A wire cable-based force transmission mechanism or the like is used to transfer the motions of each of the remotely located teleoperated actuator motors to a corresponding instrument-interfacing actuator output located on instrument carriage 75. In some embodiments, the surgical instrument 26 is mechanically coupled to a first actuator motor, which controls a first motion of the surgical instrument such as longitudinal (z-axis) rotation. The surgical instrument 26 is mechanically coupled to a second actuator, which controls second motion of the surgical instrument such as two-dimensional (x, y) motion. The surgical instrument 26 is mechanically coupled to a third actuator, which controls third motion of the surgical instrument such as opening and closing of jaws of an end effector, for example.

Figure 4:
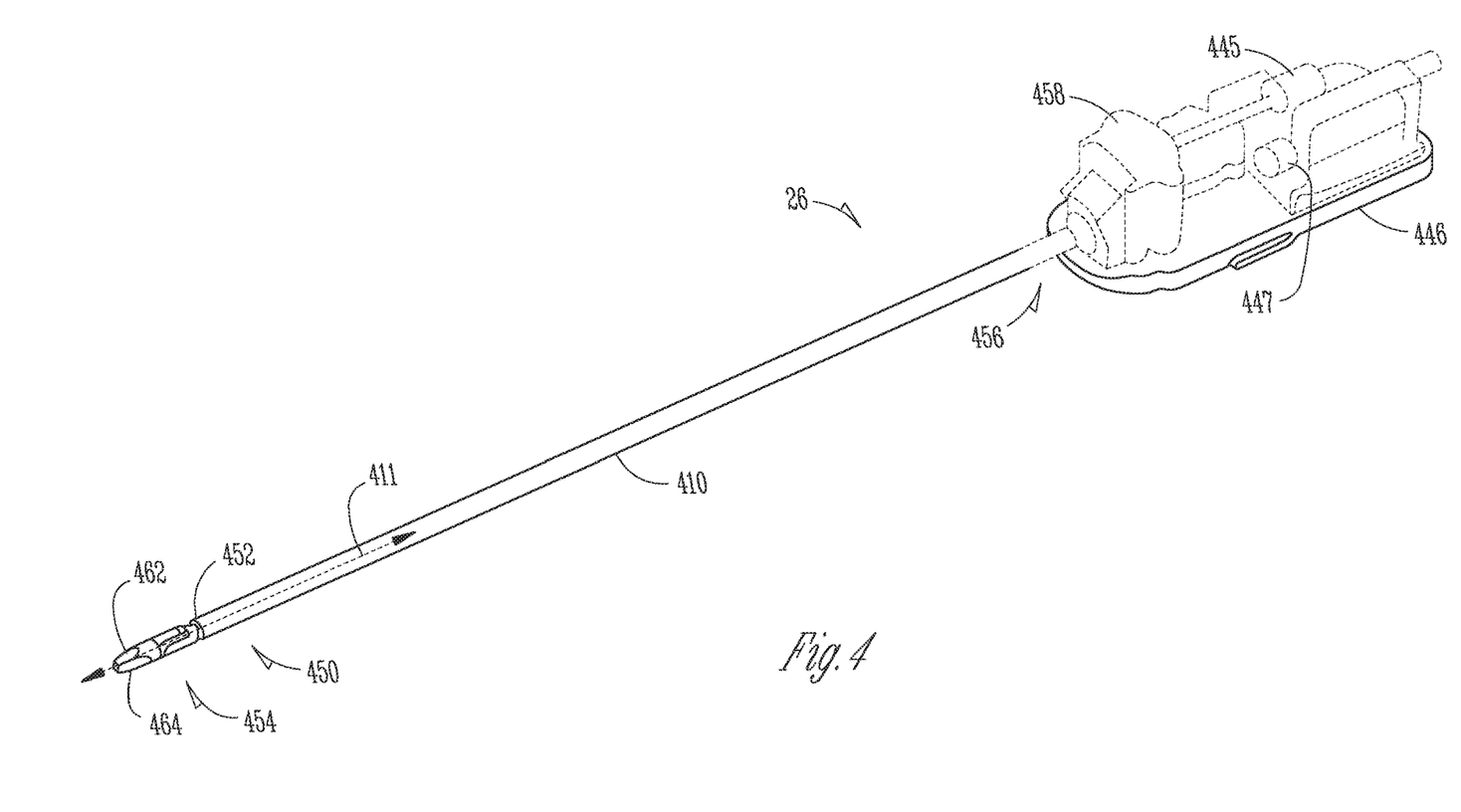
FIG. 4 is a perspective view of a surgical instrument in accordance with some embodiments.

FIG. 4 is a perspective view of a surgical instrument 26 in accordance with some embodiments. The surgical instrument 26 includes an elongated hollow tubular shaft 410 having a centerline longitudinal axis 411. The shaft 410 includes a distal end portion 450 for insertion into a patient's body cavity and proximal end portion 456 that is mechanically secured to a chassis 440 that mounts motor-driven drive elements 458 that impart forces to cables (not shown) extending within the shaft that are coupled to actuate a surgical end effector 454. A cable drive mechanism 458 may include a motor-driven spindle (not shown), for example. Actuator motors 445, 447 may be mounted on the chassis 440 itself or on the instrument carriage 75, for example. The end effector 454 is coupled to the distal end portion 450 of shaft 410 by a wrist 452. Preferably, wrist 452 provides at least two degrees of freedom. In some embodiments, the wrist 452 is rotatable about the centerline longitudinal axis 411, thereby providing three orientational degrees of freedom for surgical end effector 454 at a surgical site internal to a patient's 12 body cavity. The motor driven drive elements 458 exert forces upon the cables to impart motion to the end effector 454 such as opening or closing of jaws and (x, y) rotational motion of a wrist, for example. A variety of alternative end effectors for alternative tools may be mounted at the distal end portion 450 of the shaft 410 such as forceps, scissors, and clip applier, which include first and second end effector cantilever beams 462, 464 which pivot relative to each other so as to define a pair of end effector jaws, for example. Other end effectors, such as a scalpel and electrocautery probe may have a single end effector element, for example.

Figure 5:
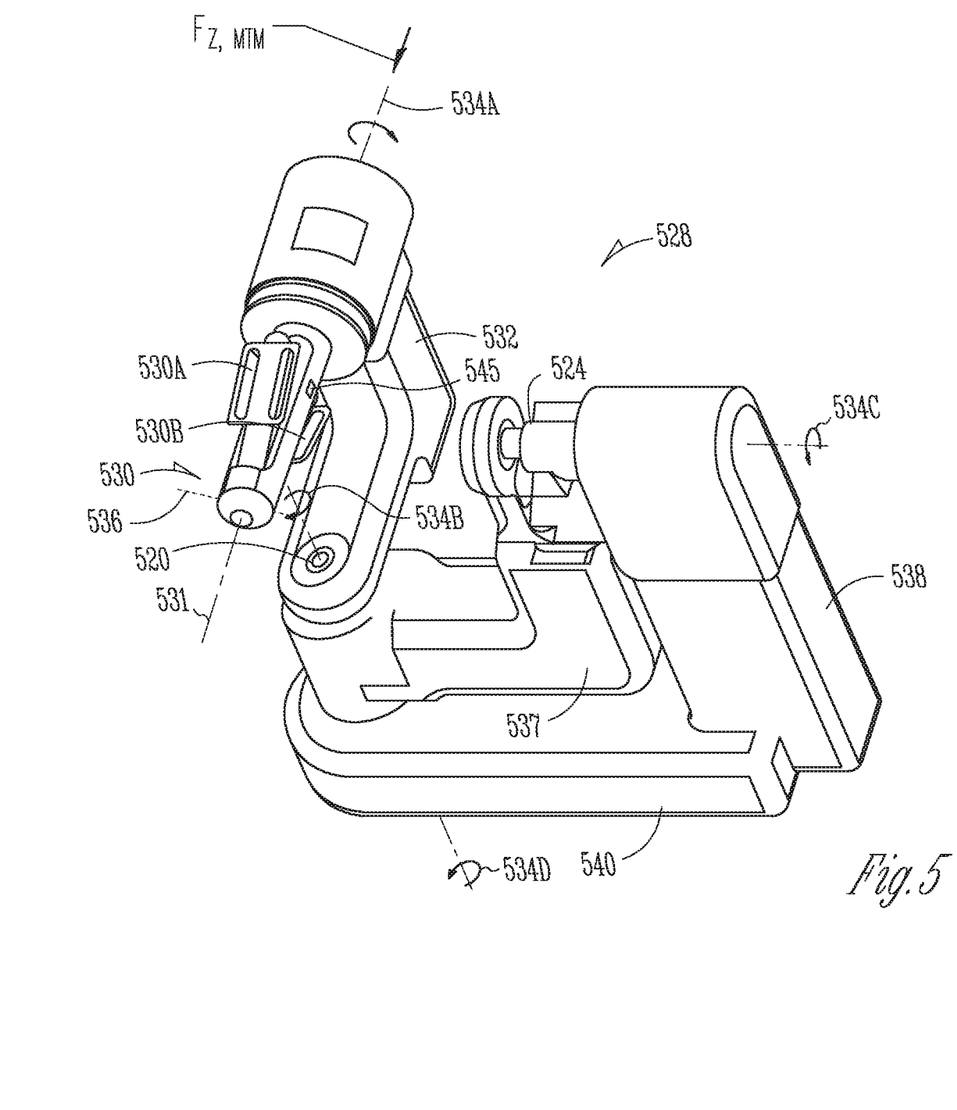
FIG. 5 is an illustrative perspective showing details of a master control input mounted upon a gimbal assembly within the surgeon consloe 16 of FIG. 2 in accordance with some embodiments.

FIG. 5 is an illustrative perspective showing details of an control input 36 mounted upon a gimbal assembly 528 within the surgeon console 16 of FIG. 2 in accordacne with some embodiments. The control input 36, which also is referred to as a master tool manipulator (MTM), includes a mount member configured as a handle 530 and first and second articulable grip members 530a, 530b mounted upon the handle 530. The handle acts as a mount member to mount the first and second grip members 530a, 530b; The first and second grip members 530a, 530b upstand at an incline from opposite sides of the handle 530. The first and second grip members are inclined relative to the handle 530 with their distal ends spaced closer together and their proximal ends spaced farther apart. The first and second grip members have an angle α between their distal ends that may vary according to forces exerted by a surgeon. In some embodiments, the angle α is an acute angle. The first and second grip members 530a, 530b are secured to the handle to articulate relative to the mount member 530. More specifically, in accordance with some embodiments, the first and second grip members 530a, 530b are secured to the handle to pivot about a master pivot axis 536 to follow a first path (not sown). A biasing member (not shown) urges the grip members 530a, 530b apart. A surgeon may grip the grip members 530a, 530b and apply forces to urge them along the first path so as to cause them to move closer together or to cause the biasing member to urge them in an opposite direction along the first path to cause them to move apart. The mount member handle 530 may include a grip actuation sensor (not shown) such as a Hall effect device to sense movement of the grip members along the first path. Finger loops may be attached to the handle to avoid slipping from the grip members. The grip members 530a, 530b are operatively coupled through kinematices, for example, to control motion of a slave end effector 454 at the distal end portion 450 of a surgical instrument shaft 410 in response to motion of the grip members 530a, 530b along th first path. The slave end effector 454 may include first and second cantilever beams 462, 464 that open and close in response to the surgeon's causing corresponding movement of the first and second grip members 530a, 530b closer together and farther apart, for example.

More particulary, in some embodiments, a four-degree of freedom gimbal 528 allows rotation of the actuatable mount member handle 530 about three axes, axis 534a, axis 534b, and axis 534c. The handle 530 is coupled to a first elbow-shaped link 514 by a first pivotal joint 16. First link 532 is coupled to a second elbow-shaped link 537 by a pivotal joint 520. Second link 537 is pivotally coupled to a third elbow-shaped link 538 by a pivotal joint 524. In some embodiments, motors of arm 538 and gimbal 528 are capable of actively applying positional and orientational forces to mount member handle 530, thereby providing tactile feedback to the surgeon. In particular, the gimbal motors can be configured through control signals to impart a feedback force $F_{Z,MTM}$ along a second path separate from the first path. In the illustrative embodiment of FIG. 5, the feedback force $F_{Z,MTM}$ is imparted parallel to an axis 531 of the handle 530 in a direction toward the vertex of the angle, which is directed perpendicular to a master pivot axis 536, such that the feedback force is felt equally by a surgeon's fingers on each of the grip members 530a, 530b. The gimbal 528 includes links 532, 537, 538. Gimbal 528 is mounted to platform 540 so as to rotate about axis 534d, and links 532, 537, 538 define additional axes 534a, 534b and 534c. Handle 530 is mounted to gimbal 528 by an actively driven joint for motion about axis 534d. Hence, gimbal 528 provides four driven orientational degrees of freedom, including a redundant orientational degree of freedom. Gimbal 528, arm 538, and the driving motors for these joints are described in more detail in U.S. Pat. No. 6,714,839, entitled "Master Having Redundant Degrees of Freedom", the full disclosure of which is expressly incorporated by this by reference.

The grip members 530a and 530b of mount member handle 530 pivot passively about a master pivot axis 536 with no drive motor provided for feedback from the slave to control their pivot. In the exemplary embodiment, an actuator 545 is mounted to generate a master grip signal indicating the angular separation between grip members 530a and 530b. In some embodiments, the actuator 545 includes a Hall effect transducer in one of the grip members and a magnet mounted in the other, so that handle 530 generates a master grip signal indicating the angular separation between grip members 530a and 530b. A biasing system urges the grip members 530a and 530b apart, and the grip members may include loops of Velcro™ or the like to more firmly position the grip members relative to a thumb and finger of a system operator. A wide variety of grip member structures might be used within the scope of the disclosure, including any surgical instrument handles, optionally including rigid or flexible loops for the thumb and/or fingers, for example. Control relationships between the grip members and slave end effector jaws is explained in more detail in U.S. Pat. No. 6,594,552, entitled, "Grip Strength with Tactile Feedback for Robotic Surgery", the full disclosure of which is expressly incorporated by this by reference.

Figure 6:
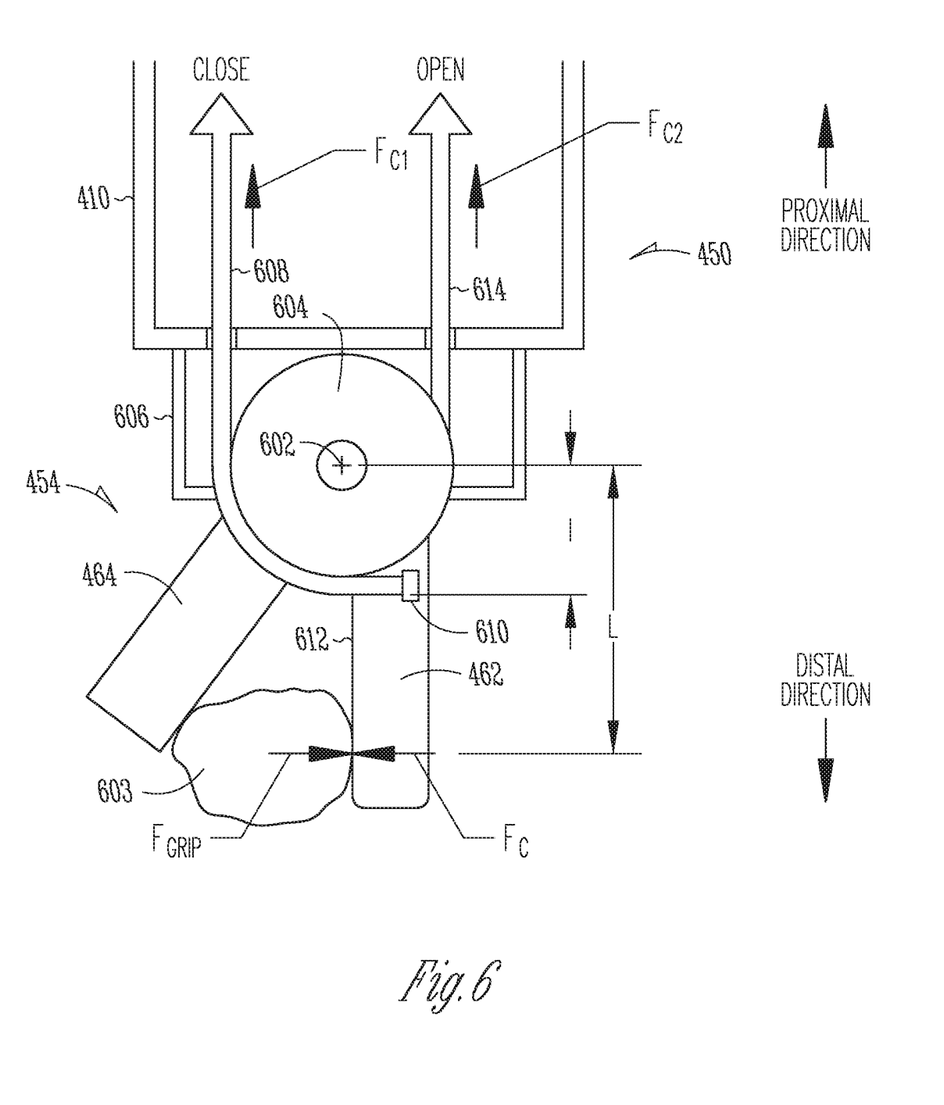
FIG. 6 is an illustrative side cross-section partially transparent view of an end effector of the surgical instrument of FIG. 4 in accordance with some embodiments.

FIG. 6 is an illustrative side cross-section partially transparent view of an end effector 454 of the surgical instrument 26 of FIG. 4 in accordance with some embodiments. The end effector 454 includes a first and second cantilever beams 462, 464 disposed at a distal end 450 of the shaft 410 of the surgical instrument 26. The first cantilever beam 462 is mounted for rotation about a slave pivot axis 602. The end effector 454 is mounted at the distal end portion 450 of the elongated shaft 410. The first and second cantilever beams 462, 464 act as first and second jaws that may be opened to capture anatomical tissue 603 between them and may be closed to grip the anatomical tissue 603 between them. The first cantilever beam 462 may act as a first jaw. The second cantilever beam 464 may act as a second jaw. In some embodiments, the first cantilever beam 462 is rotatable about the slave pivot axis 602 and the second cantilever beam 464 has a fixed position at the distal end of the shaft such that the first cantilever beam 462, acting as a first jaw, moves relative to the fixed second cantilever beam 464, acting as the second jaw. In an alternative embodiment (not shown), both the first and second cantilever beams 462, 464 may be rotatable about the slave pivot axis 602, for example. The first cantilever beam 462 that is integrally secured to a first pulley 604, which is rotatably mounted to a clevis 606 (represented by dashed lines) to rotate in unison about the slave pivot axis 602. A first cable 608 extends longitudinally within the hollow shaft 410. A proximal end (not shown) of the first cable 608 is operatively coupled to an actuator motor to impart a first cable force $F_{C1}$ upon the cable to rotate the first beam 462 toward the second beam 464 to 'close' the jaws. A distal end portion of the first cable wraps about a perimeter groove portion of the first pulley 604. An anchor 610, such as a crimp in the first cable 608, secures a distal end of the first cable 606 to the first cantilever beam so that a first cable force $F_{C1}$ exerted in a proximal direction upon a proximal end of the first cable 608 imparts a force upon the distal end of the first cable that the rotatably mounted first cantilever beam 462 translates to a rotational three $F_{C1}$ exerted at a working/tissue engagement surface 612 of the first cantilever beam 462 in a direction that is normal to the slave pivot axis 602, to urge rotation of the first cantilever beam 462 in a direction toward the second beam 464 to close the jaws.

A distal end portion of a second cable 614 that extends longitudinally within the hollow shaft 410 wraps about a perimeter groove portion of a second pulley (not shown) mounted to the clevis 606 in parallel with the first pulley 604. A proximal end (not shown) of the second cable 614 is operatively coupled to an actuator motor to impart a second cable force $F_{C2}$ upon the second cable 614 to rotate the first beam 462 awayd the second beam 464 to 'open' the jaws. A distal end of the second cable 614 is secured to the first cantilever beam 462 such that a proximal direction second cable force $F_{C2}$ exerted on the second cable 614 imparts causes the rotatably mounted first cantilever beam 462 to rotate in a direction away from the second beam 464 to open the jaws. In some embodiments the first and second cables 608, 614 include center segments that include elongated tubules and end segments that comprise wire.

During gripping of anatomical tissue 603, for example, a cable drive mechanism 458 described above, causes the first cable 608 to exert the first cable force $F_C$ axially upon the first cable 608 to a impart rotation force to the first cantilever beam 462 that balances a slave grip counter-force $F_{grip}$ imparted to the working surface 612 of the first cantilever beam 462 by the gripped tissue 603. The grip counter-force $F_{grip}$ balances the first beam force first cable force $F_C$. The balanced first cable force $F_C$ and the grip force $F_{grip}$ each produce a grip moment about the slave pivot axis, $M_{grip}$ represented in the following formulation.

$$M_{grip} = F_{grip} \cdot L = F_C \cdot l \tag{1}$$

where L represents a distance from the point where the slave grip force $F_{grip}$ is applied to the slave pivot axis, and l represents a distance from the first cable anchor 610, where the first cable 608 is secured to the first cantilever beam 462, and the slave pivot axis 602. Thus, during gripping of anatomical tissue 603, the first cable force $F_C$ has a magnitude to counter-balance the slave grip force $F_{grip}$.

Figure 7:
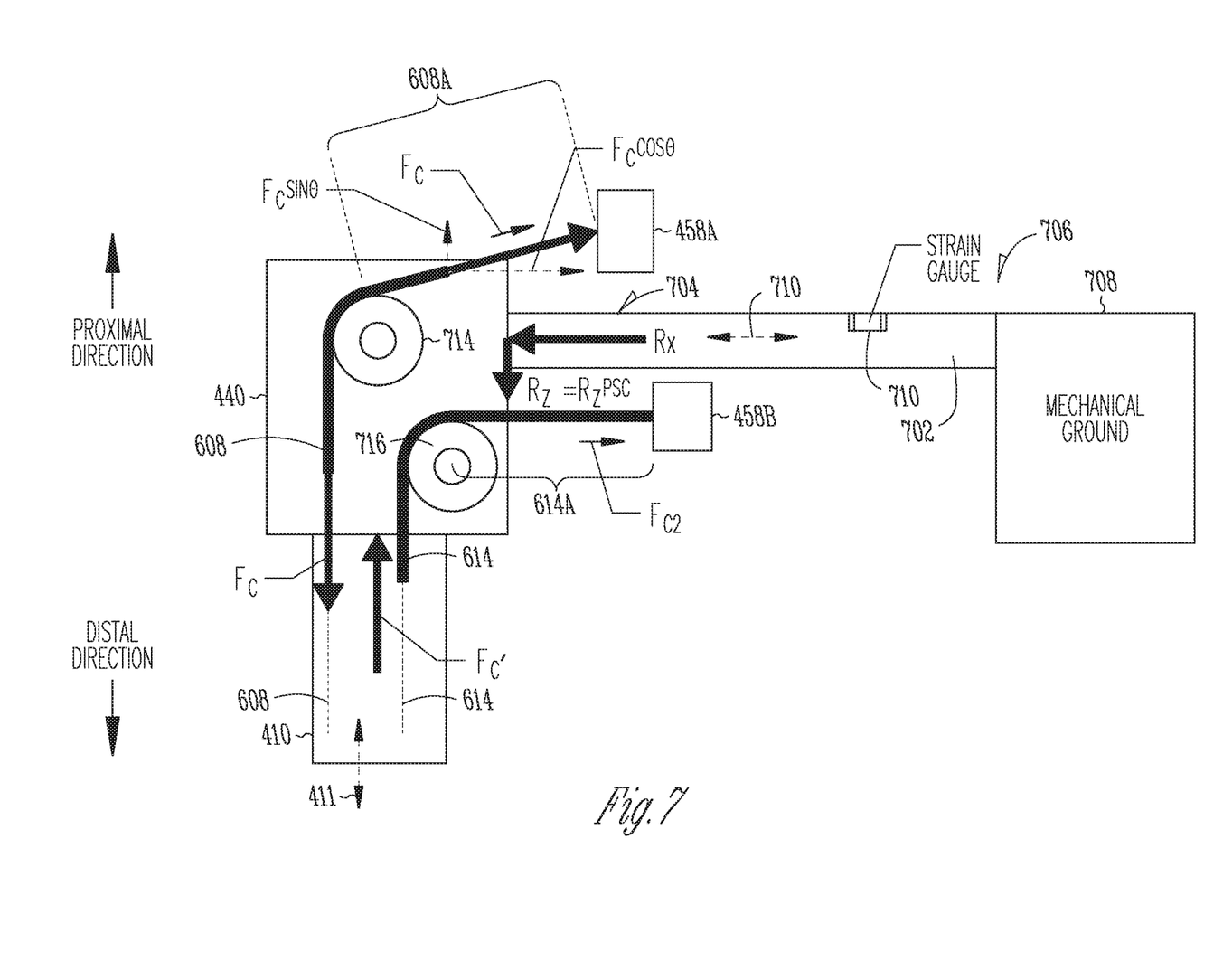
FIG. 7 is an illustrative side view of the chassis of the surgical instrument of FIG. 4 suspended from a support beam in accordance with some embodiments.

FIG. 7 is an illustrative side view of the chassis 440 of the surgical instrument 26 of FIG. 4 suspended from a support beam 702 in accordance with some embodiments. The chassis 440 is secured to the proximal end portion 456 of the shaft 410 of the surgical instrument 26. A first end portion 704 of the support beam 702 is secured to the chassis 440 and a second end portion 706 of the support beam 702 is secured to a mechanical ground 708. The support beam has a longitudinal axis 710 (the beam axis) that extends between its first and second ends 704, 706. In some embodiments, a mechanical support arm 72 acts as the mechanical ground 708. The center axis 411 of the hollow tube 410 is normal to the support beam axis 710.

A strain sensor 712 contacts the support beam 702 and is configured to measure strain imparted to the support beam 702. In some embodiments, the strain sensor includes resistive strain gauge, optical fiber Bragg grating, piezoelectric sensor. Strain is a measure of the amount of deformation of a body, such as the support beam and the strain sensor 702, due to an applied force. More specifically, strain can be defined as the fractional change of length. The mechanical ground 708 acts as a fixed reference structure that does not exhibit strain due to the cable force $F_C$ or a slave grip force $F_{grip}$.

A third pulley 714 is rotatably secured to the chassis 440. A proximal end portion of the first cable 608 wraps about a perimeter groove portion of the third pulley 714. A first cable drive mechanism 458a, which is secured to the mechanical ground 708, is configured to impart the first force $F_C$ upon the first cable 608. In some embodiments, the first cable drive mechanism 458a includes a motor driven rotatable spindle mechanically coupled to a proximal end portion of the first cable 608. The third pulley 714 and the first cable drive mechanism 458a are disposed at a vertical offset from each other relative to the support beam axis 702 such that a proximal segment 608a of the first cable 608 between them extends at an offset angle θ from the support beam axis 710. The first cable drive mechanism 458a may impart a first cable force $F_C$ to the offset angled first cable segment 608a to close the jaws. The first cable force $F_C$ applied to the offset first cable segment 608a results in a first cable offset force component $F_C \sin\theta$ upon the support beam 702 that is parallel to the shaft axis 411 and normal to the support beam axis 710 and a first cable offset force component $F_C \cos\theta$ upon the support beam 702 that is perpendicular to the shaft axis 411 and that is parallel to the beam axis 710. In reaction to the first cable force components, the support beam 702 produces reactive normal and parallel beam forces $R_X$ and $R_Z$. The reactive beam force $R_Z$, which shall be referred to herein as $F_{Z,PSC}$, the z-force measured on the system side, acts as a strain force applied at the first end 704 of the support beam 702. The strain force $F_Z$ is imparted in a direction normal to the support beam axis.

It will be appreciated that the first cable force $F_C$ imparted by the first cable within the shaft in a direction normal to the support beam axis 710 is balanced by an equal and opposite proximal-direction end effector force $F_C'$ resulting in a net force of zero upon the beam due to forces imparted to first cable segments within the shaft. Outside the shaft, however, the offset angled first cable segment 608a exerts a net force $F_C \sin\theta$ normal to the support beam and in response, the support beam produces an opposing reactive force $F_Z$.

A fourth pulley 716 is secured to the chassis 440. A proximal end portion of the second cable 614 wraps about a perimeter groove portion of the fourth pulley 716. A second cable drive mechanism 458b, which is secured to the mechanical ground 708, is configured to impart a second cable force $F_{C2}$ upon the second cable 614 to open the jaws. In some embodiments, the second cable drive mechanism 458b includes a motor driven rotatable spindle mechanically coupled to a proximal end portion of the second cable 614. The fourth pulley 716 and the second cable drive mechanism 458b are disposed level with each other without a vertical offset between them relative to the support beam 702 such no net normal force is exerted by a level second cable segment 614a extending between the fourth pulley 716 and the second cable drive mechanism 458b. The strain force $F_Z$ experienced by the support beam 702 due to the offset angled first cable segment 608a is a reactive force imparted that balances the net first cable force $F_C \sin\theta$ imparted to the support beam 702. The strain force $F_Z$ imparts a strain to the support beam 702 and to the strain sensor 712. The relationship between the net normal force $F_C \sin\theta$ and the strain force $F_Z$ imparted to the strain sensor 702 is represented by the following formulation (2).

$$F_{Z,PSC} = F_c \sin\theta + F_{cd} - F_{cp} = F_c \sin\theta = \frac{M_{grip}}{l} \sin\theta \tag{2}$$

The strain sensor produces a sensor signal $S_S$ that has a magnitude indicative of the magnitude of the strain force $F_{Z,PSC}$, which in turn is proportional to a magnitude of the grip moment $M_{grip}$ about the slave pivot axis, $M_{grip}$. In some embodiments, the signal may be a change in voltage on a Wheatstone bridge (not shown) produced by a resistance change on a strain gauge.

Figure 8:
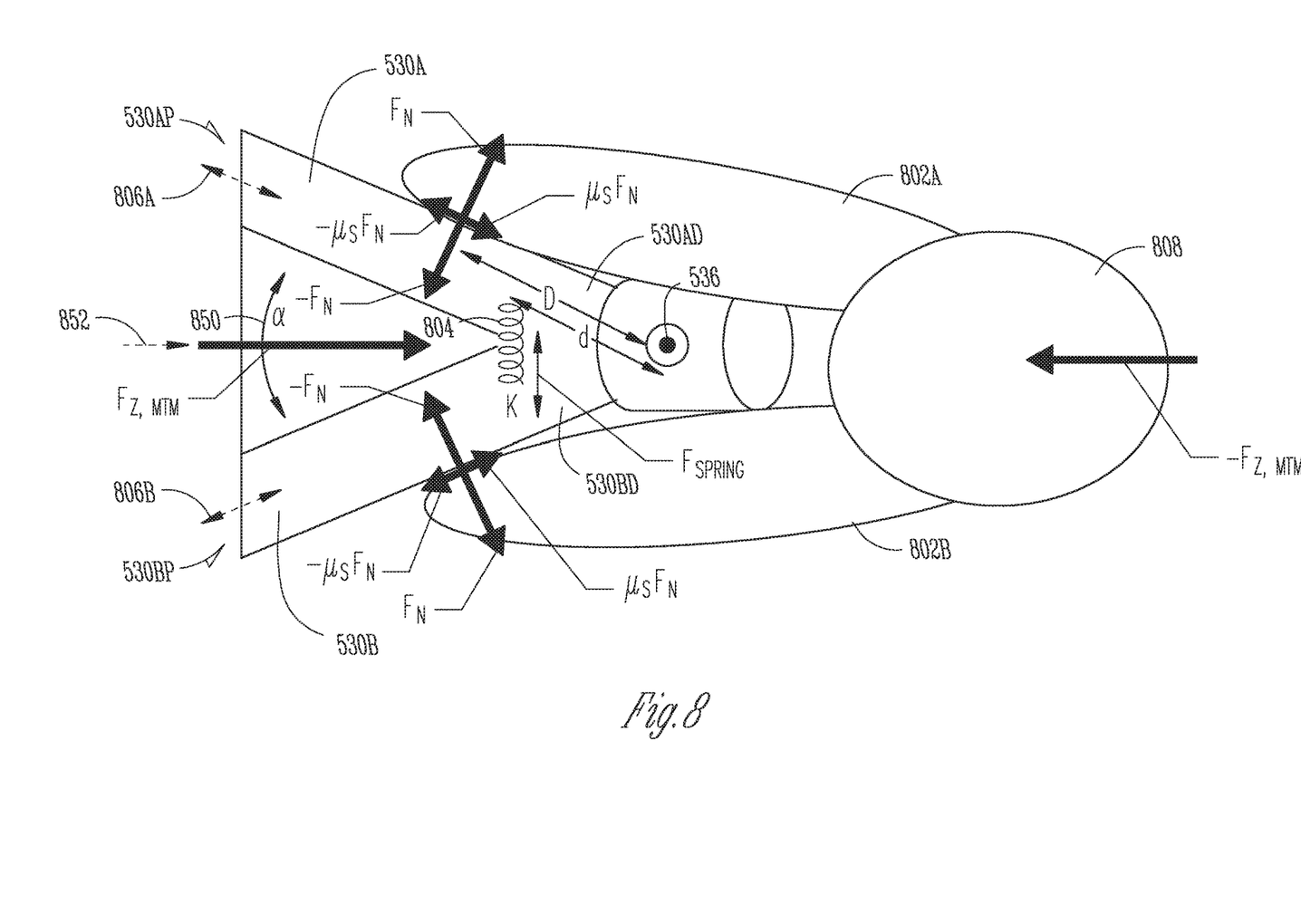
FIG. 8 is an illustrative free body diagram to show forces upon grip members of the master control input of FIG. 5 and a surgeon's fingers in accordance with some embodiments.

FIG. 8 is an illustrative free body diagram to show forces upon the grip members of a master control input and a surgeon's fingers in accordance with some embodiments. During a surgical procedure, a suraeon's fingers are placed on outside grip surfaces of the first and second grip members 530a, 530b. The first and second grip members 530a, 530b have proximal ends 530ap, 530bp and distal ends 530ad, 530bd. The distal ends 530ad, 530bd of the first and second grip members are pivotally mounted to pivot about the master pivot axis 536 and are offset from each other by an angle α. A surgeon's fingers 802a, 802b may apply fingertip forces to the first and second grip members 530a, 530b to move them along the firs path 850 about the master pibot axis 536, to move them closer together or farther apart so as to command corresponding movements of the first and second cantilever beams 462, 464 of the end effector 454. Specifically, for example, moving the proximal ends 530ap, 530bp of the first and second grip members 530a, 530b in a direction along the first path 850 to bring them closer together, which reduces the angle α between them, causes the first and second cantilever beams 462, 464 to move closer together, closing the end effector jaws. Conversely, for example, moving the proximal ends 530*ap*, 530*bp* of the first and second grip members 530*a*, 530*b* in an opposite direction along the first path 850 to space them farther apart from each other, which increases the angle α between them, causes the first and second cantilever beams to move farther apart, opening the end effector jaws. U.S. Pat. No. 6,594, 552, which is incorporated in its entirety by this reference above explains grip member control of end effectors in accordance with some embodiments. Thus, the angle α between the distal ends 530*ad*, 530*bd* of the first and second grip members determines the postions of the corresponding first and second cantilever beams at the end effector.

More particularly, a bias member, such as a bias spring 804, provides a bias force $F_{spring}$ to urge the first and second grip members 530*a*, 530*b* away from each other. A surgeon may apply forces $-F_N$, which are normal to longitudinal axes 806*a*, 806*b* of the first and second grip members 530*a*, 530*b*. The surgeon-applied force $-F_N$ rotates the first and second grip members along the first path 850 about the master pivot axis 533 to bring their proximal end portions 530*ap*, 530*bp* closer together, redcuing the angle α, between them, and commanding the imparting of the first cable force $F_C$ to cause the first and second cantilever beams 462, 464 at the end effector 454 to move closer together. Addtionally, the surgeon's fingers 802*a*, 802*b* may impart surface forces $-\mu_s F_N$, which are parallel to surfaces of the first and second grip members 530*a*, 530*b*, in cobination with the surgeon-imparted normal forces $-F_N$.

The first and second grip members 530*a*, 530*b* impart opposite direction normal forces $F_N$ to the surgeon's fingers 802*a*, 802*b* in reaction to the surgeon-imparted normal forces $-F_N$. The first and second grip members 530*a*, 530*b* also impart opposite direction surface forces $\mu_s F_N$ in reaction to the surgeon-imparted surface forces $-\mu_s F_N$.

Thus, in accordance with some embodiments, the first and second cantilever beams 462, 464 correspond to the first and second grip master members 530*a*, 530*b*. Larger scale motions imparted by a surgeon's fingers to the master members 530*a*, 530*b* are translated to corresponding smaller scale motions of the first and second cantilever beams 462, 464. In particular, in accordance with some embodiments, for example, a rotation of the master members 530*a*, 530*b* about the master pivot axis 536 is translated to corresponding rotation of the first and second cantilever beams 462, 464 about slave pivot axis 602. In some embodiments, for example, translation of movement of the master members 530*a*, 530*b* translates to corresponding movemrent of the first and second cantilever beams 462, 464 such that an angle α, about the master pivot axis 536 between the master members 530*a*, 530*b* matches an angle α slave pivot axis 602 between the first and second cantilever beams 462, 464. It is noted that during routine operation, the surgeon imparted forces and the grip member reaction forces are balanced. During routine operation, a friction force at the grip members 530*a*, 530*b* is static friction, which is just enough to match the parallel surface forces applied by the surgeon's fingers 802*a*, 802*b* at the grip members. It will be apprecated that reaction surface forces $\mu_s F_N$ are less than a maximum permitted surface friction force $F_{fr}$ at which the grip members 530*a*, 530*b* start sliding in the surgeon's fingers 802*a*, 802*b*, causing the surgeon's finger's to lose their grip, at which point the surgeon may need to apply an increased normal force to increase the surface friction to stop the sliding. The relationship between surface force $\mu_s F_N$ and maximum permitted $F_{fr}$ is represented by the following formulation.

$$F_{fr,max} = \mu_s F_N \quad (3)$$

In operation, a moment imparted by a surgeon 18 at distance a D from the master pivot axis 536 equals and is balanced by a moment imparted by the bias spring 804 at a distance d from the pivot axis 536. If it is assumed that a torsional spring has a sping force in indicated in the formulation.

$$F_{spring} = k(\alpha_0 - \alpha) \quad (4)$$

where k is the spring constant.

If it is assumed that $\alpha_0$ is the initial angular position, then the normal force $F_N$ is directly related to the angle α by the moment balance the following formulation.

$$F_N D = F_{spring} d = k(\alpha_0 - \alpha) d \quad (5)$$

Thus, $$F_N = \frac{k(\alpha_0 - \alpha)d}{D} \quad (6)$$

In view of equation (6), it will be appreciated that normal force $F_N$ cannot be modulated directly to display the grip force to the surgeon without changing the α, which would be detrimental to performance since it would affect the gripping angle of the first and second cantilever beams 462, 464 at the end effector 454. However, the inventor herein realized that a feedback surface force $F_{Z,MTM}$ imparted to mount member 530, and through it, to the first and second grip members 530*a*, 530*b* mounted thereon, along a second path 852 in a direction toward the pivot axis 533 and toward a palm 808 of the surgeon's hand may be modulated to increase a surface feedback force imparted to the fingers 802*a*, 802*b* to thereby display an indication of a magnitude of the grip force moment $M_{grip}$ at the end effector 454.

An upper limit of the feedback force $F_{Z,MTM}$ is dependent on the amount of force required to make the grip members slip against the surgeon's fingers by overcoming; static friction:

$$F_{Z,MTM} \leq 2 \cdot (F_N \sin\alpha + F_{fr,max} \cos\alpha) = 2 \cdot (F_N \sin\alpha + \mu_s F_N \cos\alpha) \quad (7)$$

$$F_{Z,MTM} \leq 2 \cdot \left(\frac{k(\alpha_0 - \alpha)d}{D}\right) \cdot (\sin\alpha + \mu_s \cos\alpha) \quad (8)$$

Since all of the values on the right are known (with the exception of the static friction coefficient, which may be estimated), this provides an upper limit for the $F_{Z,MTM}$ that can be commanded. A master-side feedback force $F_{Z,MTM}$ may be imparted along the second path 852 toward the grip members 530*a*, 530*b* in a direction perpendicular to the master pivot axis 536 to indicate a magnitude of a sensor signal $S_S$, which is indicative of the grip moment $M_{grip}$ at the slave end effector 454. Providing the master-side feedback force along the second path 852 separate from the first path 850 ensures that the user is provided an indication of magnitude of the slave force distinguishable from a bias force provided by the spring 804. Moreover, providing the master-side feedback force in a direction that is perpendicular to the master pivot axis 536 ensures that equal feedback forces are imparted to them, since in accordance with some embodiments, the grip paddles 530*a* are constrained to be symmetric. More particulalry, motors that control the gimbal assembly 528 may be controlled to impart a feedback force $F_{Z,MTM}$ to the handle 530 upon which the first and second grip members 530a, 530b are mounted that may be sensed by a surgeon through fingers 802a, 802b and that provide an indication of slave grip force $F_{grip}$. Moreover, a magnitude of the feedback force $F_{Z,MTM}$ may be modulated according to a magnitude of the sensor signal $S_S$, which is indicative of a magnitude of the grip moment $M_{grip}$ and the slave grip force $F_{grip}$.

In some embodiments, a magnitude of a surface feedbackforce transferred to the fingers 802a, 802b is the friction component of the force:

$$F_{z,MTM} = 2 \cdot (F_N \sin\alpha + F_{fr} \cos\alpha) \tag{9}$$

$$F_{fr} = \frac{F_{z,MTM}}{2 \cdot \cos\alpha} - \frac{k(\alpha - \alpha_0) d \cdot \tan\alpha}{D} \tag{10}$$

For a given angle α this friction force $F_{fr}$ felt at the fingers 802a, 802b is linear with the feedback surface force $F_{Z,MT}$ and therefore, the feedback force $F_{Z,MTM}$ can be modulated linearly to control the surface feedback friction component $F_{fr}$ of the feedack feedback force $F_{Z,MTM}$ that is felt by the surgeon and to limit the feedback friction component $F_{fr}$ to a magnitude less than an magnitude required to make the grip members 530a, 530b slip against the surgeon's fingers. Maintaining a feedback three within the upper limit ensures that finger slippage does not occur that may cause pivotal movement pivotal of the grip members 530a, 530b about the master pivot axis 536 that could be translated to movement of the cantilever beams 462, 464 about the slave pivot axis 602. In other words, the shear force upper limit ensures that a feedback force intended to a feedback force to display to a surgeon a magnitude of a slave grip force at the end effector 454 does not cause a change in rotational positions of the cantilever beams 462, 464 at the end effector 454.

Figure 9:
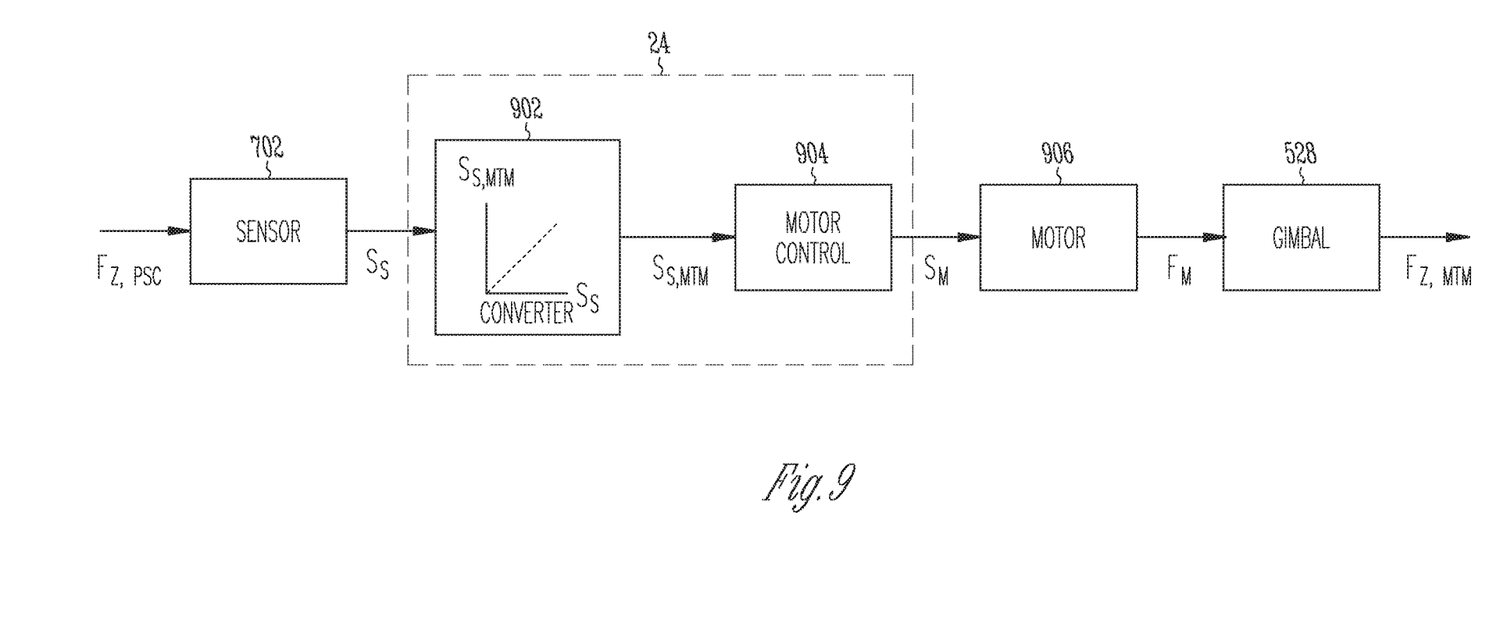
FIG. 9 is an illustrative control system flow diagram representing a transformation of a reactive beam force to a feedback force in accordance with some embodiments.

FIG. 9 is an illustrative control system flow diagram 900 representing a transformation of a reactive beam force to a feedback force in accordance with some embodiments. A reactive beam force $F_{Z,PSC}$ imparts a strain go the sensor 712, which produces a sensor signal $S_S$ having a magnitude that is proportional to a magnitude of the reactive beam force $F_{Z,PSC}$, which is proportional to a grip moment $M_{grip}$ and a slave grip force $F_{grip}$. A converter block 902 converts the sensor signal $S_S$ to a feedback force master control signal $S_{S,MTM}$. In some embodiments, the converter block 902 produces an $S_{S,MTM}$ signal having a magnitude that is a linear function of a magnitude of the sensor signal $S_S$. A motor control block 904 is configured to produce one or more motor control signals $S_M$ in response to the $S_{S,MTM}$ signal, to control motors 906 that produce threes $F_M$ to control motion of the gimbal assembly 528 to impart a feedback force $F_{Z,MTM}$ having a magnitude that is proportional to a magnitude of the $S_{S,MTM}$ signal and that is limited to avoid slippage of the first and second master grip members 530a, 530b in a surgeon's fingers. In some embodiments, the computer processors located on the electronics cart 24 are configured to determine the $S_{S,MTM}$ signal as a linear function of the $S_S$ signal. Moreover, in some embodiments, the computer processors located on the electronics cart 24 are configured to produce the one or more motor control signals $S_M$ based upon the $S_{S,MTM}$ signal. In various other embodiments, the motor control signals $S_M$ can cause an oscillating (e.g., vibrating) feedback force $F_{MTM}$ (not shown) at the master having a second path that is an oscillation path separate from the first path and having a parameter proportional to a magnitude of the $S_{S,MTM}$ signal (e.g., amplitude or frequency of oscillation of force $F_{MTM}$).

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. For example, although mechanically supported masters are depicted and described for exemplary purposes, in various embodiments the masters can be wireless or connected to the system only by wires ("ungrounded"). In one alternative embodiment, for example, a master may include a joy stick grip member mounted to a mount member, wirelessly coupled to control a slave end effector in response to movement of the joy stick. In another alternative embodiment, for example, a master may include a pistol trigger grip member in which a trigger grip member is mounted to a pistol-shaped mount member, wirelessly coupled to control a slave end effector in response to movement of the trigger. Thus, the scope of the disclosure should be limited only by the following claims, and it is appropriate that the claims be construed broadly and in a manner consistent with the scope of the embodiments disclosed herein. The above description is presented to enable any person skilled in the art to create and use a surgical system having an end effector force coupled to provide a corresponding master controller feedback force. Various modifications to the embodiments will be readily apparent to those skilled in the art, and the generic principles defined herein may be applied to other embodiments and applications without departing from the scope of the invention. In the preceding description, numerous details are set forth for the purpose of explanation. However, one of ordinary skill in the art will realize that the invention might be practiced without the use of these specific details. In other instances, well-known processes are shown in block diagram form in order not to obscure the description of the invention with unnecessary detail. Identical reference numerals may be used to represent different views of the same or similar item in different drawings. Thus, the foregoing description and drawings of embodiments in accordance with the present invention are merely illustrative of the principles of the invention. Therefore, it will be understood that various modifications can be made to the embodiments by those skilled in the art without departing from the scope of the invention, which is defined in the appended claims.

The invention claimed is:

1. A teleoperated surgical system comprising:
   a surgical instrument that includes a first jaw and a second jaw pivotally coupled to a slave pivot axis, and a sensor configured to sense a magnitude of a grip force imparted between the first and second jaws; and
   a master controller that includes:
      a first master grip member coupled to be movable about a master pivot axis along a first path, and
      a feedback generator to impart a master-side feedback force along a second path in a direction of the master pivot axis to the first master grip member;
   wherein movement of the first master grip member about the master pivot axis along the first path causes the first jaw to rotate about the slave pivot axis;
   wherein the master-side feedback force is based upon the sensed magnitude of the grip force in a direction perpendicular to the master pivot axis; and wherein the second path is separate from the first path.

2. The teleoperated surgical system of claim 1, wherein:
the first master grip member includes a longitudinal axis that extends perpendicular to the master pivot axis.

3. The teleoperated surgical system of claim 1, wherein:
the surgical instrument includes an elongated hollow shaft, one or more cables extending within the shaft, and one or more actuators;
the shaft includes a distal end portion and a proximal end portion;
the first jaw and the second jaw are pivotally coupled to the slave pivot axis at the distal end portion of the shaft;
the one or more cables are coupled to cause the first jaw to rotate about the slave pivot axis in response to one or more rotation forces imparted to the one or more cables; and
the one or more actuators are configured to impart the one or more rotation forces to the one or more cables to cause the first jaw to rotate toward the second jaw in response to movement of the first master grip member relative to the master pivot axis along the first path.

4. The teleoperated surgical system of claim 3, wherein:
the one or more actuators are configured to impart one or more cable forces to the one or more cables that balances a slave grip counter-force and
the sensor is configured to sense the magnitude of the slave grip counter-force based upon magnitude of the one or more cable forces.

5. The teleoperated surgical system of claim 4, wherein:
the teleoperated surgical system includes a support beam configured to support the first and second jaws and the shaft;
the support beam is normal to the shaft;
the sensor includes at least one strain gauge located on the support beam;
the sensor and the support beam are configured to sense the magnitude of the grip force based upon stain imparted to the support beam by the cable force; and
the cable force is angularly offset from a longitudinal axis of the support beam.

6. The teleoperated surgical system of claim 1, wherein:
the master controller further includes a second master grip member;
the first and second master grip members are pivotally coupled to one another about the master pivot axis;
rotation of the first master grip member toward the second master grip member along the first path causes the first jaw to rotate toward the second jaw;
the feedback generator is coupled to impart the master-side feedback force to the second master grip member along the second path in the direction of the master pivot axis; and
the master-side feedback force is based upon the sensed magnitude of the grip force in a direction perpendicular to the master pivot axis.

7. The teleoperated surgical system of claim 6, wherein:
the surgical instrument includes an elongated hollow shaft, one or more cables extending within the shaft, and one or more actuators;
the shaft includes a distal end portion and a proximal end portion;
the first jaw and the second jaw are pivotally coupled to the slave pivot axis at the distal end portion of the shaft;
the one or more cables are coupled to cause the first jaw to rotate about the slave pivot axis in response to one or more rotation forces imparted to the one or more cables; and
the one or more actuators are configured to impart the one or more rotation forces to the one or more cables to cause the first jaw to rotate toward the second jaw in response to movement of the first master grip member relative to a master pivot axis.

8. The teleoperated surgical system of claim 7, wherein:
the one or more actuators are configured to impart one or more cable forces to the one or more cables that balances a slave grip counter-force; and
the sensor is configured to sense the magnitude of the slave grip counter-force based upon a magnitude of the one or more cable forces.

9. The teleoperated surgical system of claim 8, wherein:
the teleoperated surgical system includes includes a support beam configured to support the first and second jaws and the shaft;
the support beam is normal to the shaft;
the sensor includes at least one strain gauge located on the support beam;
the sensor and the support beam are configured to sense the magnitude of the grip force based upon stain imparted to the support beam by the cable force; and
the cable force is angularly offset from a longitudinal axis of the beam.

10. The teleoperated surgical system of claim 6, wherein:
the first master grip member includes a longitudinal axis that has a direction component that extends perpendicular to the master pivot axis;
the master-side feedback force along the second path within the first master grip member has a direction component that extends parallel to the longitudinal axis of the first master grip member;
the second master grip member includes a longitudinal axis that has a direction component that extends perpendicular to the master pivot axis; and
the master-side feedback force along the second path within the second master grip member has a direction component that extends parallel to the longitudinal axis of the first master grip member.

11. The teleoperated surgical system of claim 6, wherein:
the feedback generator determines the master-side feedback force based upon the grip force and an angular separation between the first and second master grip members.

12. The teleoperated surgical system of claim 6, wherein:
the master controller further includes a bias member disposed to urge proximal end portions of the first and second master grip members apart from one another.

13. A surgical system comprising:
a surgical instrument that includes an end effector and a sensor; and
a master controller that includes a first input member and a second input member pivotally coupled to the first input member about a second axis, and a feedback generator;
wherein the end effector comprises a first jaw and a second jaw pivotally coupled to the first jaw about a first axis;
wherein the sensor is configured to determine a magnitude of a grip force experienced between the first jaw and the second jaw;
wherein pivoting the second input member about the second axis along a first path towards the first input member causes the second jaw to pivot about the first axis towards the first jaw; and
wherein the feedback generator generates a master-side feedback force along a second path in a direction of the second axis that is proportional to the sensed magnitude of the grip force and that has a direction component perpendicular to the second axis; and wherein the second path is separate from the first path.

14. A control method comprising:

receiving a force along a first path at a first master grip member to impart motion of the first master grip member about a first pivot axis along the first path;

imparting a rotation force to cause a first jaw, pivotally mounted to a second jaw at a second pivot axis, to rotate toward the second jaw, in response to the motion of the first master grip member about the first pivot axis along the first path;

sensing a magnitude of a grip force between the first and second jaws;

imparting a master-side feedback force along a second path in a direction of the first pivot axis to the first master grip member that is based upon the sensed magnitude of the grip force and that has a direction perpendicular to the first pivot axis; and wherein the second path is separate from the first path.

15. The method of claim 14, wherein:

imparting the rotation force to cause the first jaw to rotate toward the second jaw includes imparting one or more forces to one or more cables coupled to cause the rotation of the first jaw toward the second jaw in response to the motion of the first master grip member along the first path about the first pivot axis; and sensing magnitude of the grip force includes imparting a slave-grip counter-force to the one or more cables.

16. The method of claim 15, wherein:

sensing magnitude of the grip force includes sensing the magnitude of the grip force based upon magnitude of the slave-grip counter-force.

17. The method of claim 14, wherein:

imparting the rotation force to the first jaw, includes imparting the rotation force in response to motion of the first master grip member toward a second master grip member along the first path;

the method further includes imparting the master-side feedback force to the second master grip member along the second path based upon the sensed magnitude of the grip force; and the master-side feedback force imparted along the second path to the second master grip member has a force component perpendicular to the first pivot axis.

18. The method of claim 14, wherein:

the first master grip member includes a longitudinal axis that has a direction component that extends perpendicular to the first pivot axis; and the master-side feedback force imparted along the second path to the first master grip member has a force component in a direction parallel to a longitudinal axis of the first master grip member.

19. The method of claim 17, wherein:

the second master grip member includes a longitudinal axis that has a direction component that extends perpendicular to the first pivot axis; and the master-side feedback force imparted along the second path to the second master grip member has a force component in a direction parallel to a longitudinal axis of the second master grip member.

20. The method of claim 17, wherein:

the method includes determining the master-side feedback force based upon a grip force and an angular separation between the first and second master grip members.

* * * * *

UNITED STATES PATENT AND TRADEMARK OFFICE
CERTIFICATE OF CORRECTION

| | |
|---|---|
| PATENT NO. | : 11,666,402 B2 |
| APPLICATION NO. | : 16/753298 |
| DATED | : June 6, 2023 |
| INVENTOR(S) | : Grant M. Kadokura |

It is certified that error appears in the above-identified patent and that said Letters Patent is hereby corrected as shown below:

In the Claims

Column 14, Line 14 (Claim 9): the phrase ". . . system includes includes a . . ." should be -- system includes a --

Column 14, Line 65 (Claim 13): the phrase ". . . the first jaw; and . . ." should be -- the first jaw --

Signed and Sealed this
Eighteenth Day of July, 2023

*Katherine Kelly Vidal*

Katherine Kelly Vidal
*Director of the United States Patent and Trademark Office*